(12) United States Patent
Rosenberg et al.

(10) Patent No.: US 8,673,344 B2
(45) Date of Patent: Mar. 18, 2014

(54) SOLID DOSAGE FORM WITH A FILM CONTAINING AN ACTIVE SUBSTANCE, AS WELL AS ITS METHOD OF PRODUCTION

(75) Inventors: Jörg Rosenberg, Ellerstadt (DE); Jörg Breitenbach, Mannheim (DE); Peter Heilmann, Bad Dürkeim (DE); Helmuth Steininger, Worms (DE)

(73) Assignee: Abbvie Deutschland GmbH & Co. KG, Wiesbaden (DE)

( * ) Notice: Subject to any disclaimer, the term of this patent is extended or adjusted under 35 U.S.C. 154(b) by 246 days.

(21) Appl. No.: 12/447,506

(22) PCT Filed: Nov. 12, 2007

(86) PCT No.: PCT/EP2007/062226
§ 371 (c)(1),
(2), (4) Date: Jan. 27, 2010

(87) PCT Pub. No.: WO2008/056001
PCT Pub. Date: May 15, 2008

(65) Prior Publication Data
US 2010/0119583 A1    May 13, 2010

(30) Foreign Application Priority Data
Nov. 10, 2006   (EP) ..................................... 06123842

(51) Int. Cl.
*B29C 47/00*   (2006.01)
*B29C 47/56*   (2006.01)
*B29C 53/02*   (2006.01)
*B29C 43/24*   (2006.01)
*B29C 53/18*   (2006.01)

(52) U.S. Cl.
USPC ........... 424/443; 424/444; 424/464; 424/465; 424/468; 424/469; 424/472; 264/108; 264/109; 264/119; 264/165; 264/171.11; 264/175; 264/176.1; 264/210.1; 264/210.6; 264/211

(58) Field of Classification Search
USPC ......... 424/443, 444, 464, 465, 468, 469, 472; 264/108, 109, 119, 165, 171.11, 175, 264/176.1, 210.1, 210.6, 211
See application file for complete search history.

(56) References Cited

U.S. PATENT DOCUMENTS 3,625,214 A * 12/1971 Higuchi ........................ 424/424
4,409,206 A * 10/1983 Stricker ........................ 424/444

(Continued)

FOREIGN PATENT DOCUMENTS

DE      29 20 500 A1    11/1980
EP      0 358 107 A2    3/1990

(Continued)

OTHER PUBLICATIONS

P. Hildgen et al., "A new gradient matrix: formulation and characterization," 1995; Journal of Controlled Release, vol. 34: 263-271.*

(Continued)

*Primary Examiner* — Jane C Oswecki
(74) *Attorney, Agent, or Firm* — Saul Ewing LLP; Peter C. Lauro, Esq.

(57) ABSTRACT

The present invention relates to a solid dosage form with at least one film, which contains an active substance at least in sections, and the concentration of the active substance in the film or in the films has a gradient in a direction normal to the thickness of film. The invention further relates to a method of producing a solid dosage form, in which at least one film is produced, containing an active substance at least in sections, with the concentration of the active substance having a gradient in the longitudinal direction of the film.

20 Claims, 5 Drawing Sheets

(56) References Cited

U.S. PATENT DOCUMENTS

2005/0025831 A1* 2/2005 Lam et al. .................. 424/473
2008/0241216 A1* 10/2008 Von Falkenhausen et al. ...................... 424/426

FOREIGN PATENT DOCUMENTS

| EP | 0 872 234 | 10/1998 |
|---|---|---|
| WO | WO-98/14168 | 4/1998 |
| WO | WO-01/22947 | 4/2001 |

OTHER PUBLICATIONS

"Diffusion and Concentration Gradients", Washington University in St. Louis; Chemistry 152 [online], [retrieved Jul. 22, 2012] Retrieved from the Internet: <URL: http://www.chemistry.wustl.edu/~courses/genchem/Tutorials/Kidney/dynamic.htm>.*

P. Hildgen et al., "A new gradient matrix: formulation and characterization," 1995; J. of Controlled Release, vol. 34:263-271.*

"Density Gradient", 2000, Drugs.com [online], [retrieved Jan. 25, 2013] Retrieved from the Internet: <URL: http://www.drugs.com/dict/density-gradient.html>.*

ISR (PCT/ISA/210) issued in PCT/EP2007/062226, May 15, 2008, Abbott GmbH & Co. KG.

Hildgen, P., et al. "A New Gradient Matrix: Formulation and Characterization" *Journal of Controlled Release* 34(3): 263-271 (Jun. 1, 1995) Elsevier, Amsterdam, NL XP000505553 ISSN: 0168-3639.

* cited by examiner

SOLID DOSAGE FORM WITH A FILM CONTAINING AN ACTIVE SUBSTANCE, AS WELL AS ITS METHOD OF PRODUCTION

CROSS-REFERENCE TO RELATED APPLICATIONS

This application is the U.S. national phase, pursuant to 35 U.S.C. §371, of PCT international application Ser. No. PCT/EP2007/062226, filed Nov. 12, 2007, designating the United States and published in English on May 15, 2008 as publication WO 2008/056001 A1, which claims priority to European application Ser. No. 06123842.4, filed Nov. 10, 2006. The entire contents of the aforementioned patent applications are incorporated herein by this reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to a solid dosage form, comprising at least one film, which contains an active substance at least in sections. The invention further relates to a method for the production of a solid dosage form with an active substance.

2. Description of Related Art

There are known solid dosage forms containing an active substance, in particular pharmaceutical tablets, in which the active substance is embedded in a matrix of water-soluble, water-swellable or water-dispersible mixtures of substances. Such pharmaceutical dosage forms are also called matrix dosage forms. In such matrix dosage forms the active substance can on the one hand be released by erosion. In this case the dosage form dissolves layer by layer in an aqueous medium, thereby releasing the active substance. There is therefore a direct correlation between the decrease in weight of the dosage form and release of the active substance. On the other hand the active substance can be released by diffusion. By using polymers that are swellable in water, a layer of gel is formed on the surface of the dosage form in the matrix in contact with the aqueous medium, so that the active substance is released via this layer of gel under control by diffusion. In this case there is no direct correlation between any weight change of the dosage form and release of the active substance.

In many applications it is desirable to release the active substance in a precisely defined amount in unit time, especially in equal amount in unit time, over the duration of release of the active substance. In the case when the tablet dissolves, such a release profile can only be achieved with great difficulty, as the tablet surface changes as a function of time. Also in the case of diffusion-controlled release of the active substance, it is not possible to achieve defined release profiles with known solid dosage forms.

In addition to the dosage forms that are to be taken orally, depot dosage forms are also known, which are implanted under the skin. Such implants are used for example for hormone therapy. In most cases they comprise a polymer matrix, in which the active substance is embedded. As the polymers are biodegradable, slow erosion of the implant takes place in the body, and the active substance is slowly released. With these systems, however, there is the problem that initially there is very rapid release of the active substance located in the surfaces of the dosage form. Therefore early after implantation, release of the active substance is very high, which in many cases is a disadvantage. The initially rapid release of the active substance in dosage forms is also termed the "initial burst effect". The initial burst effect can lead to very excessive levels of the active substance immediately after implantation of a depot dosage form, which is often associated with undesirable side-effects. It is therefore desirable to produce dosage forms with which such an initial burst effect can be avoided.

Solid pharmaceutical dosage forms are produced for example by extrusion of polymer melts containing the pharmaceutical active substance. The extrudate can be shaped to the desired dosage form by calendering. Furthermore, the ground extrudate can be compacted in a tablet press, adding tableting aids if required. A method of production of pharmaceutical tablets is described for example in EP 0 358 107 A2.

A laminar dosage form and a method for its production are known from EP 0 872 234 B1. The dosage form comprises rolled or folded layers of a polymer film that contains a pharmaceutical active substance. The laminar structure of this dosage form means that diffusion of the active substance can essentially only take place at the cut edges and in the layers and out of them, so that the diffusion path is prolonged. In this way a delayed, controlled release of the active substance is achieved.

Furthermore, a solid dosage form in which a layered film is rolled up is known from U.S. Pat. No. 3,625,214. The active substance is distributed homogeneously in a matrix which is applied to a carrier film. The rate of release of the active substance can be controlled by varying the layer thickness or with an additional coating.

Finally, a pharmaceutical preparation suitable for transdermal application in the form of a film is known from DE 29 20 500 A1. The film comprises a copolymer that is compatible with the skin and is swellable in water, in which the drug is embedded in amorphous form with a defined profile. The time-dependent decrease in rate of release owing to the increase in thickness of the diffusion layer over time is compensated in the dosage form by a concentration profile of the active substance which rises in the polymer film with increasing distance from the release surface, so as to keep the rate of release of the active substance almost constant.

BRIEF SUMMARY OF THE INVENTION

The problem to be solved by the present invention is to provide a solid dosage form of the type mentioned at the beginning, with which the release profile of the active substance is adjustable. In addition, a corresponding method is to be indicated for the production of a solid dosage form with an active substance, in which the release profile of the active substance from the dosage form can be adjusted.

According to the invention, this problem is solved by a solid dosage form with the features of claim 1 and a method with the features of claim 13. Advantageous embodiments and variants can be seen from the dependent claims.

The solid dosage form of the present invention is characterized in that the concentration of the active substance in the film or films has a gradient in a direction normal to the thickness of the film.

DETAILED DESCRIPTION OF THE INVENTION

In particular the gradient proceeds in the longitudinal direction of the film. The term "longitudinal direction" means, in the sense of the invention, a direction that is normal to a vector that points in the direction of the film thickness. If the film possesses a banded form, i.e. if the extent of the film normal to the thickness is much greater in one direction than in another direction normal to the thickness, the longitudinal direction is the direction of greatest extent. If the film of the dosage form is shaped into a three-dimensional shape, the term "longitudinal direction" relates to a state of the film in which it stretches over a flat plane, and only the thickness of the film extends in a direction normal to this flat plane.

A "gradient in a direction normal to the thickness of the film or in the longitudinal direction of the film" means, in the sense of the invention, that the concentration of the active substance varies in this direction of the film, i.e. in particular the active substance is not distributed at the same concentration in this direction of the film. By selecting the gradient in a direction normal to the film thickness, the concentration of the active substance in the solid dosage form can be adjusted so that a desired release profile is achieved. Then apart from the gradient of the active substance in the film, the release profile depends additionally on film geometry, how it is present in the solid dosage form, and on the possibly space-dependent diffusion coefficient for the diffusion of the active substance in the dosage form.

It is noted that the term "concentration" as used herein is defined in the usual manner as how much active substance is present within a volume of the film. Therefore, a "gradient in the longitudinal direction of the film" means that the amount of the active substance in two volumes of the film that are adjacent to each other is different in the longitudinal direction of the film. In particular, this means that the concentration does not have only two values, namely a certain amount of active substance within the volume of the film and no active substance within a volume of the film. In this case, the film only contains active substance or not, but there is no gradient in the sense of the present invention.

As defined above, the longitudinal direction of the film is directed perpendicular to a vector that points in the direction of the film thickness. The third possible direction, which is perpendicular to the direction of the thickness of the film as well as perpendicular to the longitudinal direction of the film, is called the width of the film. According to the invention, the concentration over the width of the film is constant. Therefore, there is no concentration gradient in the direction of the width of the film. Furthermore, the width of the film containing the active substance is constant over at least the section of the film or films comprising the gradient of the active substance in the direction normal (perpendicular) to the thickness of the film and normal to the width of the film.

According to one embodiment, the active substance is embedded in a matrix of at least one water-soluble, water-swellable or water-dispersible polymer. In such systems, the concentration gradient of the active substance in the film is in particular achieved by the use of an extruder. In this case, the concentration gradient may, for instance, not be achieved by centrifugation.

According to one embodiment of the dosage form according to the invention, the latter comprises a rolled film, containing an active substance at least in sections. The dosage form is preferably formed from a rolled film. If, in a dosage form, the active substance is released primarily via the outer cylindrical surface and only negligibly via the lateral end faces and diffusion is not possible between adjacent layers of the rolled film, the active substance diffuses from the interior of the dosage form spirally in the longitudinal direction of the film outwards as far as the outer cylindrical surface, at which the active substance is released. In this way it is very easy to establish a defined release profile for the active substance by means of the gradient of the concentration of the active substance in the longitudinal direction of the film. Furthermore, such a dosage form is advantageously very simple to produce, as the concentration gradient of the active substance can be formed on a film strip, which is then rolled up or coiled up.

According to other embodiments of the dosage form according to the invention, it comprises several superposed films or one folded film. The film preferably has a uniform thickness. A dosage form with several superposed films can be used in particular as an implant.

Generally the film contains at least one water-swellable or preferably water-soluble polymer. The polymer is selected from pharmaceutically acceptable water-soluble or water-swellable polymers, especially film-forming polymers, or mixtures of such polymers. The polymers can be synthetic, semi-synthetic or of natural origin. The polymer or mixture of polymers preferably makes up at least 30 wt. % of the film.

Preferably the polymer is selected from cellulose derivatives, poly(meth)acrylates, poloxamers, polyvinyl esters, polyvinyl alcohol, protein polymers or mixtures thereof. It is also possible to use mixtures of the aforementioned polymers with up to 40 wt. % of polyvinyl pyrrolidone, relative to the polymeric constituents.

Preferred cellulose derivatives are hydroxyethyl cellulose, hydroxypropyl cellulose, hydroxypropylmethyl cellulose, hydroxypropylmethyl cellulose acetate phthalate, hydroxypropylmethyl cellulose phthalate and hydroxypropylmethyl cellulose acetate succinate.

Suitable poly(meth)acrylates are for example methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), and polymers that can be obtained under the designation Eudragit® polymers.

The so-called poloxamers are also suitable, i.e. block copolymers of polyethylene oxide and polypropylene oxide, preferably with molecular weights of at least 250 000.

Suitable polyvinyl esters are polyvinyl acetate or polyvinyl propionate. Polyvinyl alcohols of varying degree of saponification are also suitable, preferably with a degree of saponification of more than 95%.

Suitable protein polymers are gelatin or casein.

Depending on the polymer selected, release of the active substance takes place primarily by diffusion of the active substance in the film and finally via a surface to the outside or by dissolution of the dosage form inwards from the outside. Mixed forms of diffusion of the active substance from the film and dissolution of the film are also possible.

Typically the film contains at least one plasticizer, e.g. in an amount from 0.1 to 40 wt. %, preferably 0.5 to 20 wt. %.

Examples of such plasticizers are:
Long-chain alcohols, ethylene glycol, propylene glycol, glycerol, trimethylol propane, triethylene glycol, butane diols, pentanols, such as pentaerythritol, hexanols, polyethylene glycols, polypropylene glycols, polyethylene propylene glycols, silicones, aromatic carboxylic acid esters (e.g. dialkyl phthalates, trimellitic acid esters, benzoic acid esters, terephthalic acid esters) or aliphatic dicarboxylic acid esters (e.g. dialkyl adipates, sebacic acid esters, azelaic acid esters, citric and tartaric acid esters), fatty acid esters, such as glycerol mono-, glycerol di- or glycerol tri-acetate, or sodium diethyl sulphosuccinate.

Moisturizers can also be added to the film according to the invention, in order to keep the film flexible and avoid fragility or brittleness. Examples of such agents are, among others: glycerol, propylene glycol and polyglycerol esters.

According to a preferred embodiment of the dosage form according to the invention, the film does not include a carrier layer. In this case the film containing the active substance can for example be shaped into the desired geometric shape directly, and in particular it can be rolled up.

According to another embodiment of the dosage form, the film comprises a carrier layer, in particular a carrier layer that does not contain an active substance, on which a layer containing an active substance is applied. The carrier layer can be formed for example from a water-soluble and/or water-swellable polymer. All of the polymers mentioned above can be used.

Furthermore, the carrier layer can be formed from a water-insoluble polymer. For example, the following polymers can be used: polyolefins such as polyethylene, polypropylene; polyvinyl chloride; polyvinyl acetate. Preferably ethyl cellulose is used.

When the dosage form comprises a rolled film, the concentration of the active substance preferably increases from sections of the film located radially outwards to sections of the film located radially inwards. In particular, with a dosage form that dissolves during use, this means that despite decreasing surface area of the dosage form during dissolution in unit time, quantitatively a constant amount of active substance is released.

The concentration gradient of the active substance can be stepwise or stepless, i.e. the change in concentration of adjacent points in the longitudinal direction of the film can be constant or variable. Finally the concentration gradient of the active substance can be linear or nonlinear, i.e. the concentration can vary linearly or nonlinearly over the length of the film. Preferably the concentration gradient of the active substance in the film is selected in such a way that the release profile of the dosage form is linear, and in particular constant, in a time interval that is relevant for the release of the active substance.

Furthermore, the concentration gradient of the active substance in the film can be selected so that the release profile of the dosage form possesses characteristics with time-delayed release of the active substance ("pulsatile release"). For example, the section on the outside of the film of the dosage form might not contain active substance. In this case the active substance diffuses through this section on the outside of the film first, before it is released.

A further embodiment of the invention is a dosage form that releases the active substance over a period of time in a controlled, increasing dose. This is suitable, for example, for the administration of active substances to which patients develop an acute tolerance. An acute tolerance is manifested by a shortened duration and a decrease in intensity of the therapeutic effect. Release in an increasing dose can compensate for the acute tolerance and maintain the desired therapeutic effect.

According to a preferred variant of the dosage form according to the invention, a barrier layer is applied to the film to prevent diffusion of the active substance between adjacent layers of the film. If for example the film is coiled up into a spiral in the dosage form, the barrier layer prevents partial diffusion of the active substance radially outwards even during storage so that the gradient is reduced, instead of spirally in the longitudinal direction of the film.

The barrier layer generally contains at least one polymer. The polymer is selected from pharmaceutically acceptable polymers, especially film-forming polymers, or mixtures of such polymers. Polymers in which the active substance is insoluble or only sparingly soluble are especially preferred. The polymers can be synthetic, semi-synthetic or of natural origin. The polymer or mixture of polymers preferably makes up at least 30 wt. % of the barrier layer.

Preferably the polymer is selected from cellulose derivatives, poly(meth)acrylates, poloxamers, polyvinyl esters, polyvinyl alcohol, protein polymers or mixtures thereof. It is also possible to use mixtures of the aforementioned polymers with up to 40 wt. % of polyvinyl pyrrolidone, relative to the polymeric constituents.

Preferred cellulose derivatives are hydroxyethyl cellulose, hydroxypropyl cellulose, hydroxypropylmethyl cellulose, hydroxypropylmethyl cellulose acetate phthalate, hydroxypropylmethyl cellulose phthalate and hydroxypropylmethyl cellulose acetate succinate.

Suitable poly(meth)acrylates are for example methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), and polymers that can be obtained under the designation Eudragit® polymers.

The so-called poloxamers are also suitable, i.e. block copolymers of polyethylene oxide and polypropylene oxide, preferably with molecular weights of at least 250 000.

Suitable polyvinyl esters are polyvinyl acetate or polyvinyl propionate. Polyvinyl alcohols of varying degree of saponification, preferably with a degree of saponification of more than 95%, are also suitable.

Suitable protein polymers are gelatin or casein.

According to another preferred embodiment of the dosage form according to the invention, the film has at least two layers, the first layer having a concentration gradient of a first active substance and the second layer a concentration gradient of a second active substance. In this way it is possible to provide combination dosage forms, from which the individual active substances are released at different rates.

The film contains in particular one pharmaceutical active substance. Active ingredients are biologically active agents and include those which exert a local physiological effect, as well as those which exert a systemic effect, after oral administration.

Examples of suitable active substances include, but are not limited to:

analgesic and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime and streptomycin;

anti-coagulants such as warfarin;

antidepressants such as amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenyloin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; farnesyl transferase inhibitors; farnesyl transferase inhibitors; anthrachinon derivatives such as mitoxantron;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, rilu-zole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, amprenavir, nevirapine, efavirenz, delavirdine, indinavir, nelfinavir, saquinavir, adefovir and hydroxyurea;

beta-adrenoceptor blocking agents such as atenolol, carvedilol, metoprolol, nebivolol and propanolol;

cardiac inotropic agents such as amrinone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;

disinfectants such as chlorhexidine;

diuretics such as acetazolamide, furosemide, hydrochlorothiazide and isosorbide;

enzymes;

essential oils such as anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol and thyme;

gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;

haemostatics such as aminocaproic acid;
lipid regulating agents such as atorvastatin, lovastatin, pravastatin, probucol and simvastatin;
local anaesthetics such as benzocaine and lignocaine;
opioid analgesics such as buprenorphine, codeine, dextromoramide, dihydrocodeine, hydrocodone, oxycodone and morphine;
parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;
peptides and proteins such as antibodies, becaplermin, cyclosporine, tacrolimus, erythropoietin, immunoglobulins and insuline;
sex hormones such as estrogens: conjugated estrogens, ethinyloestradiol, mestranol, oestradiol, oestriol, estrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone and quingestanol acetate;
stimulating agents such as sildenafil, vardenafil;
vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;
vitamins such as vitamins of the A group, the B group, including B1, B2, B6 and B12 and nicotinic acid and nicotinamide and compounds with vitamin B-like properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group.
their N-oxides, their pharmaceutically acceptable acid or base addition salts and their stereochemically isomeric forms.

In the method according to the invention, the active substance is preferably embedded in a matrix of water-soluble, water-swellable or water-dispersible polymer.

Pharmaceutically acceptable acid addition salts comprise the acid addition salt forms which can be obtained conveniently by treating the base form of the active ingredient with appropriate organic and inorganic acids.

Active ingredients containing an acidic proton may be converted into their non-toxic metal or amine addition salt forms by treatment with appropriate organic and inorganic bases.

The term addition salt also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

In the method according to the invention for the production of a solid dosage form with an active substance, at least one film is produced, which contains an active substance at least in sections, with the concentration of the active substance of the film or films having a gradient in a direction normal to the thickness of the film, especially in the longitudinal direction of the film. The film or films containing active substance are then shaped into the dosage form. The film containing the active substance is in particular rolled up to give the dosage form. Furthermore, the film containing the active substance can be formed from several superposed films to produce the dosage form or can be folded to produce the dosage form.

According to a preferred embodiment of the method according to the invention, the film is produced without solvent, in particular without organic solvent. In this case subsequent drying of the film is no longer necessary. Moreover, solvents often have a toxic effect on humans. As such solvents are preferably not used in the dosage form according to the invention, it is better tolerated.

According to one example of application of the method according to the invention, the film is formed by an extrusion process comprising feeding a mixture of at least one polymer and the active substance into an extruder, and varying the mixing ratio of the active substance to the polymer during the extrusion process, i.e. depending on the desired concentration gradient of the active substance in the film. In particular the aforementioned polymers can be used. The mixture exiting the extruder is typically forced through at least one film nozzle or slit die to form the film.

According to one embodiment of the method according to the invention, the film can be produced without a carrier layer for the layer containing the active substance. According to another embodiment, a carrier layer, and especially a carrier layer not containing active substance, is used for making the film, and a layer containing active substance is applied on this. For example, the film can be formed by coextrusion, producing the carrier layer by means of a first extruder and producing a layer containing active substance by means of a second extruder, controlling or regulating the volume flows of the two extruders during coextrusion in such a way that the extruded film containing the active substance has the desired concentration gradient of active substance. The concentration gradient of the active substance can be formed in the direction of extrusion during extrusion or coextrusion. Additionally, during extrusion or coextrusion, the concentration gradient of the active substance can be formed transversely to the direction of extrusion. In the latter case, for example, a multichamber feeder can be used.

According to a variant of the method according to the invention, the film containing the active substance is laminated with one or more laminating layers. The laminating layer is in particular a barrier layer, which prevents diffusion of the active substance between adjacent layers in the formed film of the dosage form. Furthermore, the laminating layer can be in the form of an adhesive layer or separating film for adjacent sections of film in the dosage form. The extruded film containing the active substance can for example be laminated by feeding it in the plastic state to a calender together with the laminating layer or layers. Furthermore, prior to lamination, another active substance can be applied in or on the laminating layer.

According to a further embodiment of the method according to the invention, first a carrier film is formed as a carrier layer, and is coated with a dispersion or suspension of the active substance containing solvent. The carrier layer can for example be produced by a film extrusion process.

Figure 1:
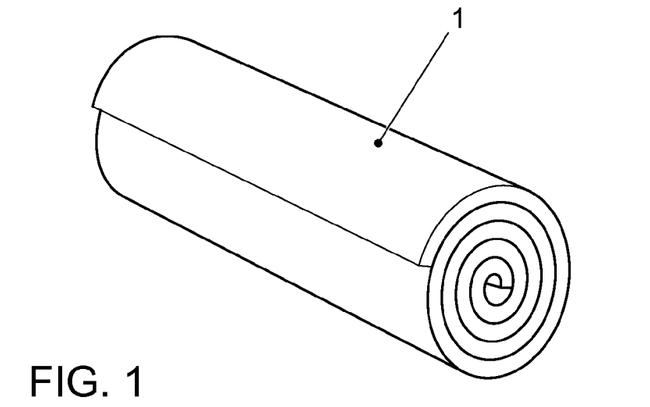
FIG. 1 shows an example of application of the dosage form according to the invention.

FIG. 1 shows the basic structure of the dosage form. It comprises a film 1, which is rolled up to form a cylindrical body, in which film 1 forms a spiral. Film 1 contains an active substance, the concentration of which varies along the spiral.

Film 1 thus has a concentration gradient of the active substance in the longitudinal direction of the film.

Figure 2:
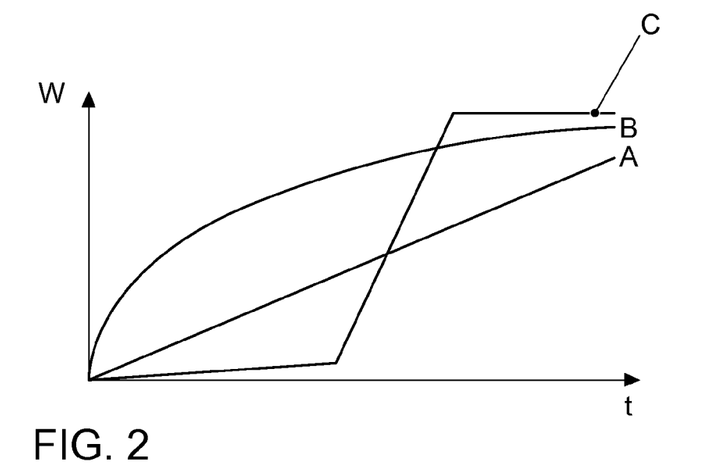
FIG. 2 shows various release profiles of the active substance.

The precise form of the concentration gradient depends on the desired release profile of the active substance when the dosage form is administered as intended. FIG. 2 shows various release profiles of the active substance, i.e. The time-dependent variation in release of the active substance W. Curve A shows a linear release profile, curve B shows a nonlinear release profile, and curve C shows a release profile with time-delayed initial release of the active substance ("pulsatile release"). The axis "t" stands for a function of time.

Figure 3A:
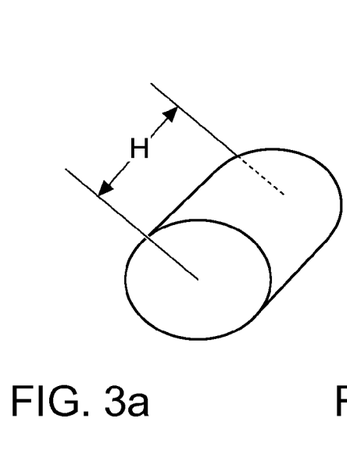
FIGS. 3a and 3b serve for explaining a simplified calculation of a concentration gradient of the active substance.
Figure 3B:
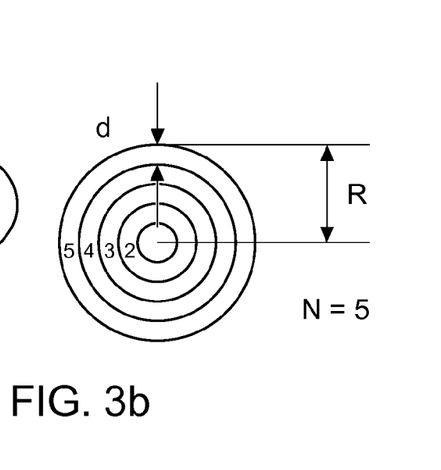

The concentration gradient of the active substance required for the dosage form can be calculated for a desired release profile of the active substance. In particular, the surface/volume ratio of the basic geometric shape of the dosage form is taken into account. The manner of adjustment of the concentration gradient of the active substance is shown below, based on a calculation with simplifying assumptions and referring to FIGS. 3A and 3B:

The cylindrical dosage form has radius R, height H and a total of N layers, the thickness of the single layer being $d=R/N$. For the calculation it is assumed as a simplification that the coiled body is not wound continuously, but is composed of individual layers, as shown in FIG. 3B.

It is further assumed that the film containing the active substance and forming the dosage form dissolves, releasing the active substance. It is further assumed that the radius of the coiled body decreases by an individual layer, i.e. by the thickness d in unit time. The following is found for the volume of the innermost layer:

$$V_i = 2 \cdot \pi \cdot d^2 \cdot L$$

The following is obtained for the volume of the i-th layer:

$$V_1 = \pi \cdot d^2 \cdot L \cdot (2 \cdot i - 1)$$

where L is the length of the layers. The coiled body dissolves from the side. Its height decreases by 2d in unit time, so that the length L of the layers varies as follows:

$N$-th layer: $L = H$ $(N-1)$-th layer: $L = H - 2d$ $(N-i)$-th layer: $L = H - 2d \cdot (N-i)$ Hence it follows that during dissolution, the instantaneous volume of each outermost layer is as follows:

$$V_i = \pi d^2 \cdot (H - 2d \cdot (N-i)) \cdot (2 \cdot i - 1)$$

At point of time t, not only layer t dissolves, but also the lateral end faces of all layers with indices i<t. These end faces of thickness D have a volume of:

$$V_i^{St} = \pi \cdot d^2 \cdot d \cdot (2 \cdot i - 1)$$

At first, each layer t has an unknown concentration of active substance $\rho_t$. By time t, therefore, the following amount of active substance $X_t$ will be released. Release is made up of the component of the outermost layer and the component of the lateral end faces:

$$X_t = \rho_t \cdot V_i + 2 \sum_{i=1}^{t-1} [V_i^{St} \cdot \rho_t]$$

$$X_t = \rho_t \cdot \pi \cdot d^2 \cdot (H - 2d(N-i)) \cdot (2i-1) + 2 \sum_{i=1}^{t-1} [\rho_i \cdot \pi \cdot d^2 \cdot d \cdot (2i-1)]$$

If we predefine the amount of active substance released, i.e. if we predefine the amount of active substance $X_t$ for the point of time t, the above set of equations can be solved for the unknown $\rho_t$, starting at t=1 and determining $\rho_1, \rho_2, \rho_3, \ldots$, one after another. Then the coiled body can be made from the individual layers with the calculated concentrations of active substance $\rho_i$. Simplifying once again, a strip of film containing the active substance can be produced which comprises successive pieces each having the length of a coil circumference and each containing the calculated concentration of active substance $\rho$.

The concentration gradient of the active substance can be calculated even more accurately by calculating a continuous, spiral-shaped coil. Such calculations are familiar to a person skilled in the art. Again in this calculation, the volumetric concentration of active substance in the dosage form will be determined so that constant dissolution of this body from the outside produces the desired release of the active substance over time. Then the required appearance of the concentration of the active substance in a strip, which is rolled up to form the coiled body, is found by calculating back from the spatial distribution of the active substance thus calculated.

Figure 4:
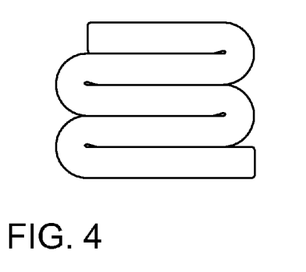
FIG. 4 shows another example of application, in the dosage form according to the invention.
Figure 5:
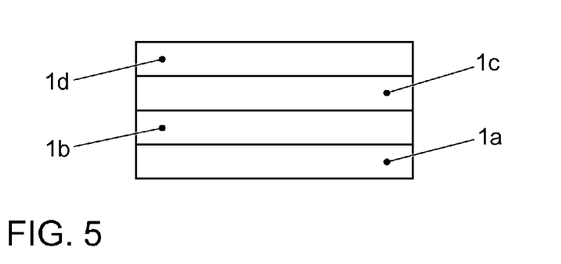
FIG. 5 shows a further example of application of the dosage form according to the invention.

Two more examples of the dosage form according to the invention are shown in FIGS. 4 and 5. In the example shown in FIG. 4, film 4 is folded, so that it is essentially rectangular in cross-section. In the example shown in FIG. 5, the dosage form comprises several superposed films 1a to 1d.

Further details of the dosage form will be explained below in connection with the description of the method of production.

The films containing the active substance can be produced by coating a carrier film with a solution or suspension of the active substance in a volatile solvent, which also contains a polymer. Solvent-free production is preferred, however, especially by extrusion.

For example, the film can be produced in the so-called film extrusion process, as described e.g. in Ullmann's Encyclopedia of Industrial Chemistry, 6th edition, 1999 Electronic Release; Section: "Films". In this case the underlying polymer or polymer blend, if necessary with other additives, is plasticated in an extruder. The plasticated polymer melt is discharged from the extruder through a wide-slit nozzle and is led over several smoothing rolls, which may be heated, producing a film of the desired width and thickness. Extrusion of the polymer is carried out in co-rotating twin-screw extruders, if necessary with addition of other additives. These additives may for example possess softening properties, in order to lower the processing temperature of the polymers. Low-molecular polyethylene glycols, triethyl citrate, triacetin and water are suitable here. The processing temperatures can be controlled over a relatively wide range simply by means of the water content of the polymers used. Polymers with a water content of 0.5-12 wt. %, preferably 1-8 wt. %, and especially of 2-5 wt. % are suitable. The water content of the polymer can be determined by known methods (e.g. by IR drying of a sample and determination of the weight loss, or by Karl Fischer titration). As all of the aforementioned polymers are slightly hygroscopic, a defined water content can be achieved by storing the polymers in the open at a defined humidity of the air in accordance with the known sorption isotherm of the polymer. Moreover, the required amount of water can be applied to the polymer, generally in powder form, by means of known granulation techniques prior to extrusion. It is, however, simplest, and therefore especially preferred, to feed the required water at the same time as powder feed of the polymer by means of a constant-feed fluid pump. This direct feed can similarly also take place with the aforementioned other suitable (and also liquid) plasticizers. The methods for feed of liquid additives into an extruder are known to a person skilled in the art.

Then the active substance, dissolved or suspended in an aqueous or non-aqueous solvent, is applied in a uniform layer thickness on the carrier film. This can be effected by known methods, for example as described in F. Hensen (Ed.): Plastics Extrusion Technology, 2nd edition, Hanser Publishers, Munich, 1997, pages 391-394. Solvents are preferred which possess a low boiling point, can be removed almost completely without expensive processes and are not toxic in the amounts that are left behind on the film. For example, ethanol, isopropanol or tetrahydrofuran can be used as solvents.

Figure 6:
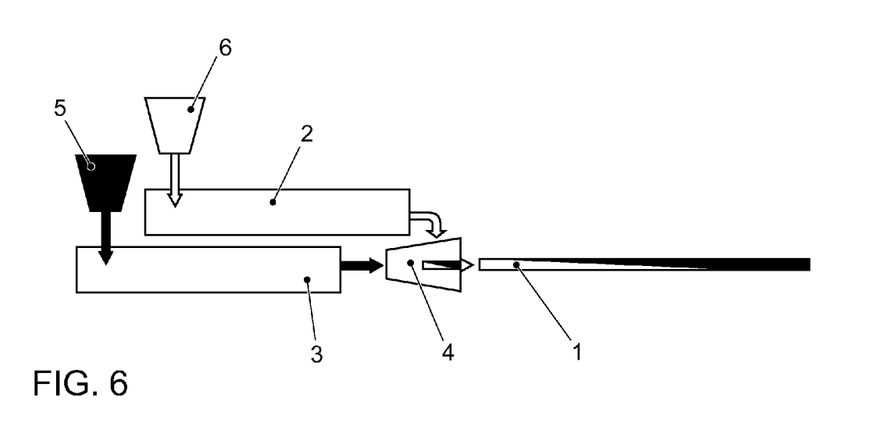
FIG. 6 shows another device for carrying out the method according to the invention.

The concentration gradient of the active substance on the film can be produced in particular by means of extrusion techniques. Equipment for coextrusion is shown in FIG. 6. In this equipment, the material of the carrier film via a first feeder 6 is produced in a first extruder 2, and a mixture containing the active substance, which can be processed thermoplastically, is produced in a second extruder 3 via a second feeder. Both melt streams from extruders 2 and 3 are led simultaneously into a coextrusion nozzle 4. The gradient of active substance on film 1 is controlled by varying the volume flows of the individual extruders 2 and 3, preferably keeping the total volume flow constant over time, in order to produce a film with constant thickness.

The films produced in this way are coiled or rolled into a dosage form. The dosage form is thus cylindrical, and there is a concentration gradient of the active substance between the layers on the outside and those in the interior of the dosage form. So that, on the one hand, these coiled layers stick together and thus keep the coiled layers together, and on the other hand so as to minimize diffusion of the active substance and possibly of other constituents of the dosage form between the coiled layers, additional layers are applied, e.g. by laminating, to the films before they are rolled together.

The laminating technique is known to a person skilled in the art (cf.: Ullmann's Encyclopedia of Industrial Chemistry, 6th edition, 1999 Electronic Release; Section: Films, and F. Hensen (Ed.): Plastics Extrusion Technology, 2nd edition, Hanser Publishers, Munich 1997, pages 365-398). Once again, two variants may be considered in particular, namely solvent-free laminating and laminating with solutions or suspensions.

Figure 7:
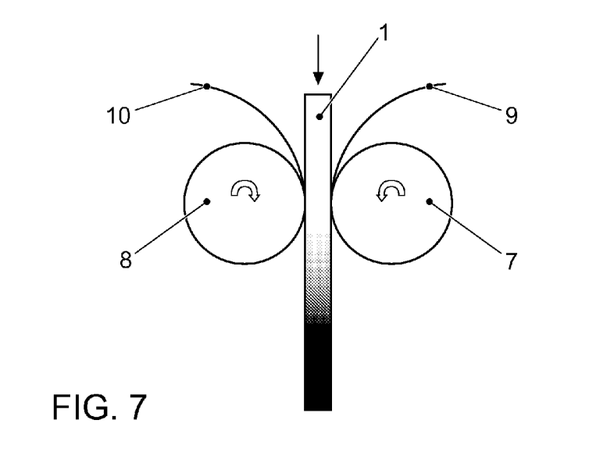
FIG. 7 shows, schematically, a portion of a device that is used when carrying out the method according to the invention.

As shown in FIG. 7, in solvent-free laminating the film 1 produced by the aforementioned methods, containing the active substance in the form of a gradient, is fed directly after extrusion, i.e. in the still plastic state, into a calender with two rolls 7 and 8, in particular a smooth-roll calender, into which one or two films 9 and 10, which form the laminate layers, are fed simultaneously. This method is similar to the method for coating calendered tablets already described in U.S. Pat. No. 5,897,910. With this method it is possible to apply firmly adhering laminate layers on films containing active substance that are still in the plastic state. A great many films of pharmaceutically acceptable polymers can be considered as the laminate material, such as are described in U.S. Pat. No. 5,897,910. If two films are used, in principle it is possible to use two different laminate films. For example, the first film could perform the function of diffusion barrier layer, while the other film promotes adherence of the complete film during coiling.

In principle, the same techniques can be used in laminating with solutions or suspensions as in the case of application of the layer containing the active substance (F. Hensen (Ed.): Plastics Extrusion Technology, 2nd edition, Hanser Publishers, Munich, 1997, p. 391ff.). This method is suitable especially when very thin layers are to be applied (e.g. as an adhesive layer), or when temperature-sensitive materials do not allow a thermal process to be used.

There are other possibilities for production of dosage forms with special properties, in that the films used for laminating can contain one active substance or several active substances. For example, it is possible to produce combination dosage forms, from which the individual active substances are released at different rates. This is achieved in that both the layer used as carrier film and the layers used for laminating contain the active substance in the form of a gradient.

Figure 8:
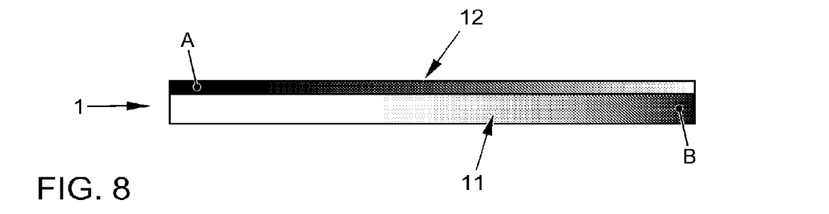
FIG. 8 shows a carrier film with a laminating layer.

The resultant film 1 is shown in FIG. 8. It comprises a carrier film 11 with a concentration gradient of active substance B and a laminate layer 12 with a concentration gradient of an active substance A.

With the method described above, any desired concentration gradients of the active substance can be produced, as were described previously.

The dosage form can then be manufactured from the film with the concentration gradient of the active substance. If the film already possesses the desired height of the dosage form, it can be rolled up in the longitudinal direction, and then the concentration gradient of the active substance also runs in the longitudinal direction. If a wide film was produced, it can first be cut into strips, which are then rolled up. Once again the concentration gradient of the active substance runs in the longitudinal direction, i.e. in the direction of coiling. If necessary the strips that are to be rolled up are moistened prior to rolling, or are provided with another kind of adhesive, so that they hold together firmly. Furthermore, the film can—as described above—be stacked or folded in a zigzag. The dosage forms can be stamped from a stack of films.

According to a further embodiment, soluble or insoluble films can be wound between the film containing the active substance, for deliberately influencing the release of the active substance as a function of time.

According to a further embodiment, the calculated gradient of the active substance in the film can also be approximated by assembling the film strip from individual film sections, each containing different amounts of the active substance. This results in a stepped profile in the film, which approximately reproduces the calculated gradient. In this case it is possible for example to use a carrier film, on which the individual partial sections with different concentrations of active substance are applied.

Figure 9:
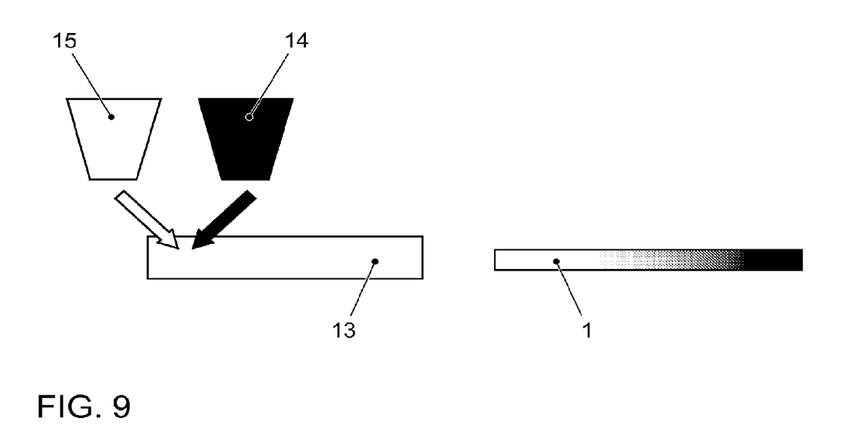
FIG. 9 shows, schematically, a device for carrying out the method according to the invention.

A further, especially preferred example of application dispenses with the use of a carrier film. Equipment for production of a film of this kind, containing an active substance, is shown in FIG. 9. It comprises an extruder 13, to which a mixture of a polymer, the active substance and other additives if required, is fed. The active substance is fed to the extruder 13 via a first weigh feeder 14, and the other constituents of the mixture via a second weigh feeder 15. During extrusion, the feed rates of the two weigh feeders 14 and 15 are varied, preferably with the total feed rate as the sum of the two weigh feeders 14 and 15 remaining constant, to give a constant mass flow in extruder 13 throughout the operating time. The result is a film 1 without carrier, having a concentration gradient of the active substance. This film 1 can be rolled up directly as the dosage form. In addition the film—as described previously—can be laminated and provided with a barrier layer.

Figure 10:
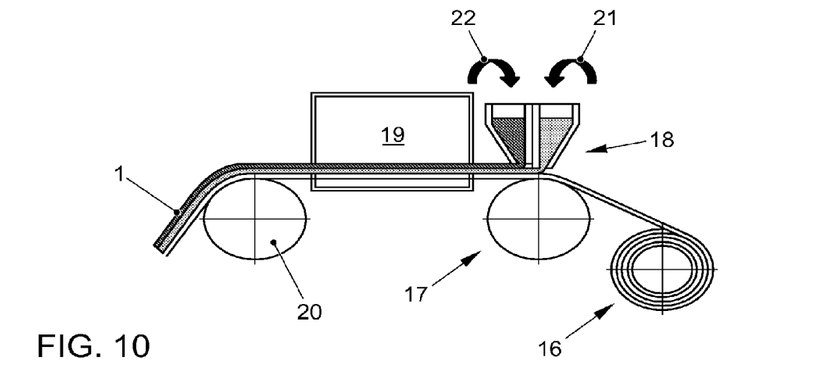
FIG. 10 shows a double feeder, which is used in one example of application of the method according to the invention.

Alternative embodiments for applying or incorporating the active substance are described below:

Similarly to extrusion, the films can also be produced by coating solvent-containing dispersions or suspensions of the active substance. Coating equipment suitable for this is shown in FIG. 10. It comprises a film unwinding device 16, a coating device 17, a feeder 18, a dryer 19 and a winding device 20 for the coated film 1. Feeder 18 is in the form of a double feeder, from which a solution 21 and a solution 22 can be applied to the starting film.

Figure 11:
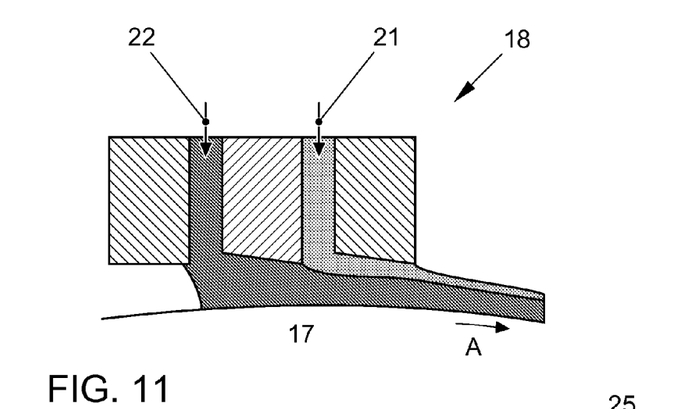
FIG. 11 shows a pouring drum, which is used according to an example of application of the method according to the invention.

A section through feeder 18 is shown in FIG. 11. With feeder 18, two layers can be applied simultaneously to one carrier film. By omitting one pouring channel, a single layer can be produced in the same way. Moreover, additional pouring channels can be added, for applying more than two layers. As shown in FIG. 11, the coating device 17 is designed as a coating roll. The carrier film passes over this coating roll, which moves in the direction of arrow A in FIG. 11. Solutions 21 and 22 with the dispersed active substance are fed to the coating roll, and the layer thickness of the cast film can be adjusted by selecting the distance between feeder 18 and the coating roll or by appropriate pre-metering. If the concentration of active substance is altered in one or in both dispersions during coating, a concentration gradient of the active substance in the longitudinal direction of the film is obtained, while the total thickness remains constant. In this way it is possible to establish any desired profiles of active substance in the longitudinal direction of the cast layer.

Figure 12:
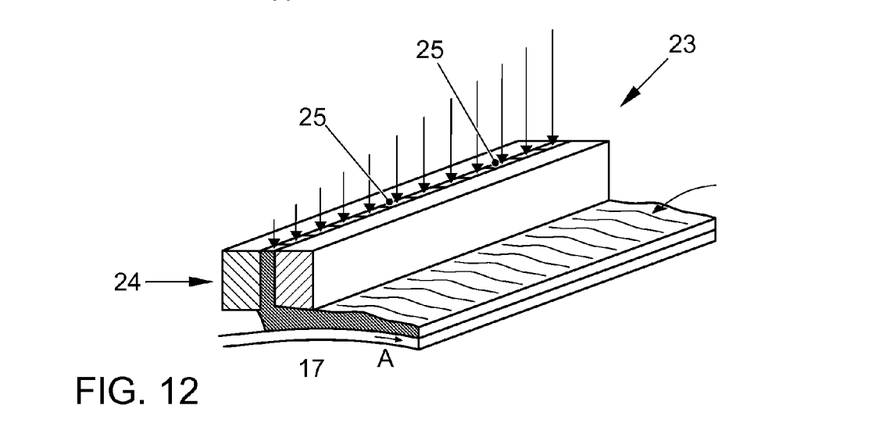
FIG. 12 shows a multichamber feeder, which is used according to an example of application of the method according to the invention.

According to an alternative embodiment, the film is produced with the multichamber feeder 23 shown in FIG. 12. As with the double feeder shown in FIG. 10, a coating device 17, which is constructed as a coating roll, rotates in the direction of arrow A. A coating can be applied on the carrier film by means of feeder 24. Feeder 24 has a large number of chambers 25, which run transversely to the longitudinal direction of the film and to the direction of rotation of the coating roll. If chambers 25 are filled with dispersions with different content of active substance, a concentration gradient of the active substance is produced transversely to the direction of coating. If after drying the film is then cut into strips transversely to the direction of coating, a concentration gradient is again obtained in the longitudinal direction of the strip. This strip can then be rolled, folded or stacked to give the dosage form.

Figure 13:
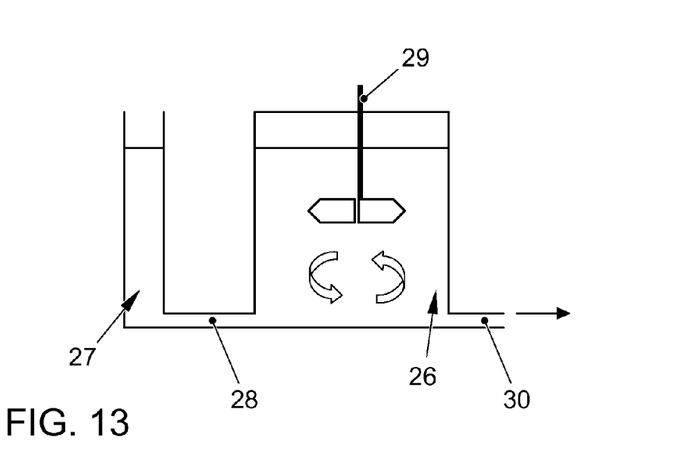
FIG. 13 shows another device, which is used according to an example of application of the method according to the invention.

According to a further embodiment, the carrier film is coated with a solution or suspension of the active substance in a volatile solvent, which simultaneously contains a polymer, using the equipment shown in FIG. 13. In this case a suspension with water has the advantage that the water does not have to be removed, as it acts as a plasticizer. The equipment comprises two tanks 26 and 27. Tank 26 contains a solvent, and tank 27 contains a solvent containing the active substance. The two tanks 26 and 27 are joined together via channel 28. A stirrer 29 is provided in tank 26. The solution containing active substance used for coating travels via outlet 30 to the carrier film. Because the two tanks 26 and 27 are connected to one another, the concentration of the active substance in the solution used for coating increased continuously during emptying of the compound vessel comprising two individual tanks. Almost any desired concentration gradients of the active substance can be produced depending on the volumes of the two containers, which are different, and depending on the concentration of the active substance in tank 27. Moreover, further variation of the concentration gradient is possible for special geometric shapes of tanks 26 and 27. Tanks 26 and 27 could, for example, have a conical geometry.

According to a further embodiment, films containing active substance are produced by pumping the active substance as solution or as suspension into an extruder, in which the polymer is plasticated. The liquid incorporated by addition of the solvent can be removed again even during extrusion, e.g. by a vacuum shaft just before the nozzle outlet. By varying the liquid feed over time, a concentration gradient of the active substance can be incorporated in the film extrudate. In that case the total dose, i.e. the mass flow leaving the extruder via the nozzle, should remain constant throughout, in order to produce a film of constant thickness.

According to a preferred variant, the total feed of liquid also remains constant throughout production. This can be achieved by varying the concentration of the active substance in the solution or in the suspension over time. In this variant it is advantageous if several solvents (also and especially water) act as plasticizers with concentration-dependent action for the polymers used, so that if the feed of liquid does not remain constant, continuous adjustment of the parameters of the extrusion process would be required (especially the temperatures of the shots). If liquid feed remains constant, extrusion can be carried out with constant process conditions.

According to one example, 1.5 kg/h of a powder mixture comprising hydroxypropyl cellulose (Klucel® EF/Aqualon, 80 wt. %) and Copovidone (Kollidon® VA-64/BASF, 10 wt. %) are plasticated continuously in a twin-screw extruder (18 mm screw diameter) and discharged via a wide-slit film nozzle (approx. 20 cm discharge width). In addition, an aqueous solution of metoprolol tartrate is fed at a constant 6 g/min into the extruder via an HPLC pump, so that the concentration of active substance increases from 0% continuously (linearly) to 40 wt. % within an extrusion time of 10 minutes. In the penultimate shot before the discharge nozzle, the extruder contains a vacuum mandrel, with which a vacuum (10-200 mbar) can be applied. In this way, the solvent (water) that was fed in can be removed from the melt. The discharged film contains metoprolol tartrate at a concentration increasing from 0 to a maximum of 8.8 wt. %.

Feed of the active substance from a solution or suspension, with removal of the entrained solvent by application of vacuum directly to the plasticated melt is in many cases preferred to the coextrusion process with two extruders operating simultaneously, as it is simpler from the standpoint of process engineering. Especially in the case of temperature-sensitive active substances, liquid feed is suitable, because the added solvent (water, ethanol, isopropanol, THF; preferably: water or lower alcohols; especially preferred: water) acts as a plasticizer and the process temperatures can therefore be lowered ("gentle extrusion"). In conjunction with the production of implants, where the active substances are generally highly active peptides/proteins, this production process is often preferred to embedding of these often temperature-sensitive peptides/proteins in polymer matrices.

If contents of active substance in the films are required to exceed about 10 wt. %, in many cases suspensions are preferred to solutions for pump feeding, for only then is it possible to deliver a sufficiently large amount of active substance (the solubility of many active substances is not high enough, especially in water). To avoid sedimentation in the suspensions, either known suspension stabilizers can be added (among others, water-swellable polymers suitable for pharmaceutical use) and/or the suspensions must be stirred continuously.

EXAMPLES

A. Coating of a Carrier Film

Comparative Example A

A thin PVA (polyvinyl alcohol) carrier film was coated with a thick polyvinyl acetate layer, which contained the dissolved active substance. The thickness of the carrier film was 50 µm, and the thickness of the layer containing the active substance was 200 µm. The water-soluble xanthene dye Rhodamine 6G, which has good solubility in polyvinyl acetate and can be detected reliably by optical means, was selected as the model substance. The films were rolled up to form rolls with a length of 15 mm and a diameter of 10 mm. These dosage forms were dissolved in 0.1N HCl (gastric juice) at 37° C. and the amount of active substance released was determined by inline VIS spectroscopy with a transmission sensor.

Figure 14:
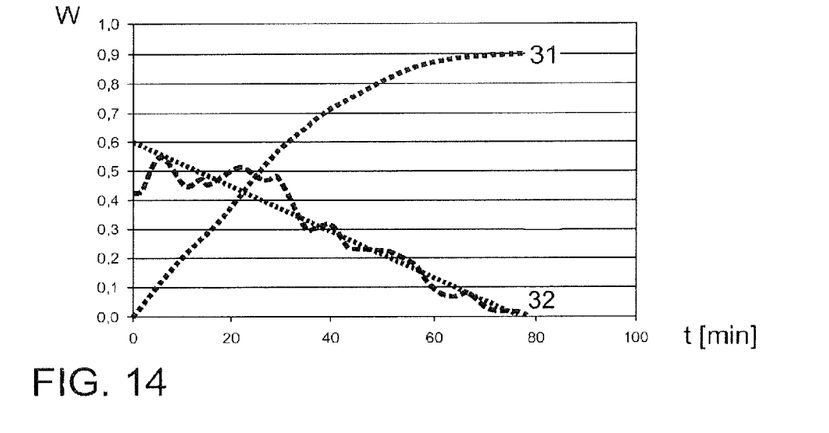
FIG. 14 shows the time-dependent variation in release of the active substance in a comparative example.

In this comparative example, a dosage form was produced from a film with a constant distribution of active substance of 35 g/cm³. The release of active substance W plotted as a function of time is shown in FIG. 14. Curve 31 shows the cumulative amount of active substance, and curve 32 shows the release of the active substance measured as a function of time. It was found that the release of active substance decreased over time.

Example A1

Comparative example A was repeated, except that the concentration of active substance in the film was calculated in such a way that a release profile that is constant over time should be established in the rolled-up state of the dosage form. The dimensions of the dosage form corresponded to those in the comparative example. The active substance was applied in three zones or steps, in which concentration gradients of 0.04%/mm, 0.16%/mm and 0.92%/mm were established. The total amount of active substance in the dosage form was 33 mg.

Figure 15:
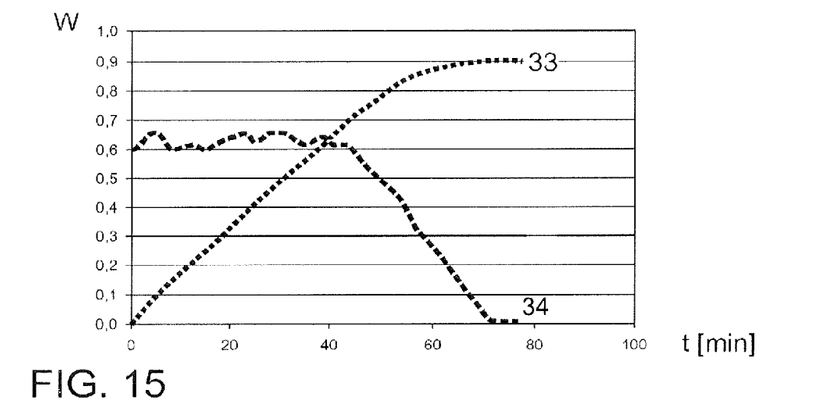
FIG. 15 shows the time-dependent variation in release of the active substance in an example according to the invention.

The release of active substance W is plotted as a function of time in FIG. 15. In this case, curve 33 shows the cumulative amount of active substance and curve 34 shows the measured release of active substance over time. The desired linear, time-constant release profile is obtained, at least for the first 40 minutes of release of the active substance.

Example A2

A dosage form with diffusion-controlled release was produced, in which a water-insoluble carrier film was used, so that the active substance could only be released via the end faces of the roll, and in particular not via the generated surface of the roll. Cellulose diacetate was used as the carrier material. The concentration of active substance applied in the dosage form was a constant 35 mg/cm³.

Figure 16:
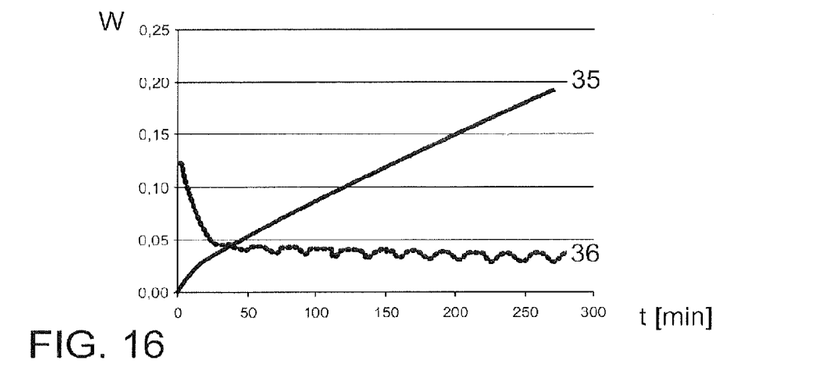
FIG. 16 shows the time-dependent variation in release of the active substance according to another example according to the invention.

FIG. 16 once again shows the release of active substance as a function of time, with curve 35 showing the cumulative amount of active substance and curve 36 the measured release of active substance over time. There is relatively slow release of the active substance over 5 hours, with a very constant release profile over time. There is, however, a very pronounced initial burst effect, but this can be eliminated by adjusting the gradient.

B. Production of Film by Extrusion

Comparative Example B

A homogeneous powder mixture, comprising 30 wt. % hydroxypropyl cellulose (type Klucel EF, from Hercules) and 70 wt. % Copovidone (Kollidon VA-64, BASF) was metered at a constant feed rate of 1.5 kg/h via a weigh feeder (from K-tron, gravimetric feed) into the feed opening of a co-rotating twin-screw extruder. A homogeneous melt was discharged from the extruder via a film nozzle (width 8 cm) mounted at the outlet, and could be rolled to form a film over smoothing rolls. The dosage form was formed from this film.

Example B1

The test was conducted as in comparative example B, but this time in addition to feed of the polymer mixture as in comparative example B, ibuprofen in solid form (powder) was added to the active substance via a second weigh feeder. The feed rate of the second weigh feeder was increased steadily over time, until the weight ratio of the two powder streams from weigh feeder 1 (polymer mixture) and weigh feeder 2 (ibuprofen) corresponded to a value of 4 parts to 1 part. As in comparative example B, it was possible to produce a film from the melt containing the active substance by smooth rolling, and the dosage form could be formed from that.

Example B2

The test was conducted as in example B1, but this time the active substance (ibuprofen) was fed in molten form via a heated gear pump directly into the extruder. The feed rate of the pump was increased steadily over time, until the weight ratio of the two powder streams from weigh feeder 1 (polymer mixture) and weigh feeder 2 (ibuprofen) corresponded to a value of 4 parts to 1 part. As in example B1, it was possible to produce a film from the melt containing the active substance by smooth rolling.

The invention claimed is:

1. A method of producing a solid dosage form comprising an active substance, the method comprising:
 a) feeding the active substance to an extruder via a first weigh feeder;
 b) feeding simultaneously with the feeding of step a) one or more additives to the extruder via a second weigh feeder;
 c) varying feed rates of the first weigh feeder and the second weigh feeder, respectively;
 d) producing via extrusion a film without a carrier layer so that the active substance is present in a concentration gradient within the film; and
 e) forming the film containing the active substance into a dosage form, thereby forming a solid dosage form comprising the active substance.

2. The method according to claim 1, characterized in that the concentration gradient runs in a longitudinal direction of the film that is normal to a thickness of the film, wherein an amount of the active substance is present in two volumes of the film that are adjacent to each other and the amount in each volume is different in the longitudinal direction of the film.

3. The method according to claim 1, characterized in that the film containing the active substance is rolled or folded to form the dosage form.

4. The method according to claim 1, wherein the additives of step b) comprise a water-soluble, water-swellable, or water-dispersible polymer, and the film of step d) contains the active substance embedded in a matrix of the polymer.

5. The method according to claim 1, wherein, in step c), a total feed rate of the first weigh feeder and the second weigh feeder is constant.

6. The method according to claim 1, wherein width of the film is constant over the section(s) of the film comprising the active substance present at the concentration gradient along the longitudinal direction.

7. The method according to claim 6, wherein the active substance is present at a constant concentration over the width of the film.

8. The method according to claim 1, wherein the film has a uniform thickness.

9. The method according to claim 1, wherein the concentration gradient of the active substance is formed transversely to an extrusion direction.

10. The method according to claim 1, wherein said extrusion is essentially solvent-free.

11. A method of producing a solid dosage form comprising an active substance, the method comprising:
   a) feeding one or more additives to a first extruder, thereby producing a first melt stream;
   b) feeding a mixture comprising the active substance to a second extruder, thereby producing a second melt stream;
   c) varying volume flows of the first and second melt streams from the extruders respectively, and feeding the first and second melt streams simultaneously into a co-extrusion nozzle;
   d) producing through co-extrusion a film containing the active substance present in a concentration gradient within the film; and
   e) forming of the film containing the active substance into the dosage form.

12. The method according to claim 11, wherein the film does not contain a carrier layer.

13. The method according to claim 11, wherein the concentration gradient of the active substance runs in a longitudinal direction of the film that is normal to a thickness of the film, wherein an amount of the active substance is present in two volumes of the film that are adjacent to each other and the amount in each volume is different in the longitudinal direction of the film.

14. The method according to claim 11, wherein the film containing the active substance is rolled or folded to form the dosage form.

15. The method according to claim 11, wherein the co-extrusion is essentially solvent-free.

16. The method according to claim 11, wherein a total volume flow of the first and second melt streams is kept constant.

17. The method of claim 11, wherein the film has a constant thickness.

18. The method of claim 11, wherein the method comprises a step of feeding the film obtained from step d) into a calendar with two rolls, and wherein the film is in a plastic state.

19. A solid dosage form comprising an amount of an active substance produced in accordance with the method of claim 1.

20. A solid dosage form comprising an amount of an active substance produced in accordance with the method of claim 11.

* * * * *